US00PP11258P

United States Patent [19]

Lee

[11] Patent Number: Plant 11,258

[45] Date of Patent: Feb. 29, 2000

[54] PLUMCOT TREE NAMED 'MIWANG'

[76] Inventor: Yun-Won Lee, 133-14, ChoJung-Lee, JungPyong-Eup, KeoSan-Gun, ChungBuk, Rep. of Korea

[21] Appl. No.: 08/910,780

[22] Filed: Aug. 13, 1997

[51] Int. Cl.[7] ..... A01H 5/00

[52] U.S. Cl. ..... Plt./180

[58] Field of Search ..... Plt./38.1, 39, 184, Plt./186, 180

*Primary Examiner*—Howard J. Locker
*Assistant Examiner*—Melissa L. Kimball
*Attorney, Agent, or Firm*—Gilberto M. Villacorta; Pepper Hamilton LLP

[57] ABSTRACT

A new and distinct variety of plumcot tree (apricot×plum) which is a heavy and regular producer of fruit; with half-open growth habit; producing firm, dark red fruit overspread with yellowish spots; with the fruit having good handling and shipping qualities, high brix values (18% average), excellent flavor and eating quality, and purplish red to dark flesh; the fruit ripening in middle season (late July); the stone being very small; and the fruit being semi-clingstone.

5 Drawing Sheets

ORIGIN OF THE VARIETY

The new and distinct variety of plumcot (apricot×plum) tree was originated by me in my orchard, which is located near JungPyong, KeoSan, ChungBuk, Korea, from seedlings selected from a large numer (about 1500 seeds) of seedlings obtained from native Apricot (*Prunus armeniaca*) seeds in HeongSung, Kangwondo, Korea, that resulted from open-pollinated flowers near a native plum (*Prunus domestica*) tree. These seedlings were grown under careful observation by me, giving the characteristics of the apricot, except for two trees. One of these two seedlings is the present variety of plumcot tree, this particular seedling having shown the specially desirable and novel characteristics of a plumcot. I propagated the selected hybrid variety in anticipation of ultimate introduction to the fruit growing industry.

ASEXUAL REPRODUCTION OF THE VARIETY

The present variety of plumcot tree was asexually reproduced by me in my experimental orchard by budding, and all reproductions run true to the original tree in all respects.

SUMMARY OF THE VARIETY

The present new and distinct variety of plumcot tree has been denominated 'Miwang', and is of medium size, half open growth and is a regular and productive bearer of medium, red skin with yellowish spots, dark red to red purple flesh, semi-clingstone fruit with a mild, very sweet flavor with excellent eating and stock quality. The fruit is further characterized by having firm flesh, the ability to remain on the tree 7 to 10 days after maturity (shipping ripe), having good handling and shipping quality, a red skin ground color overspread with attractive yellowish spots and ripening in the middle maturity season, approximately 20 to 30 days after native plums, which are grown in Korea such as Jadusalgu, Notably, the stone of the fruit is about ⅔ smaller than that of the native plum, and so the flesh of the fruit of the present invention is especially abundant for a fruit of this size, since the stone is small. The new plumcot variety is pollinated by bees.

DESCRIPTION OF THE PHOTOGRAPHS

The accompanying photographs show typical specimens of the fruit and foliage of my new variety tree.

Figure 1:
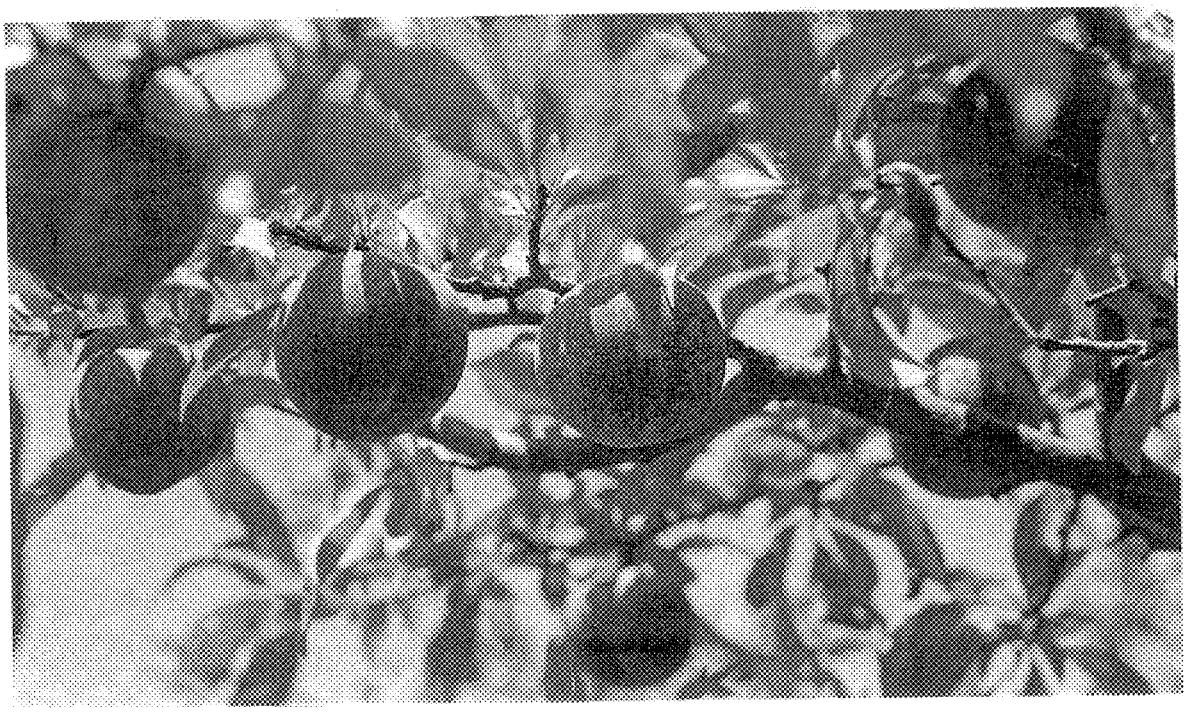
FIG. 1 shows a typical specimen of the foliage and fruit of the new and distinct plumcot variety.
Figure 2:
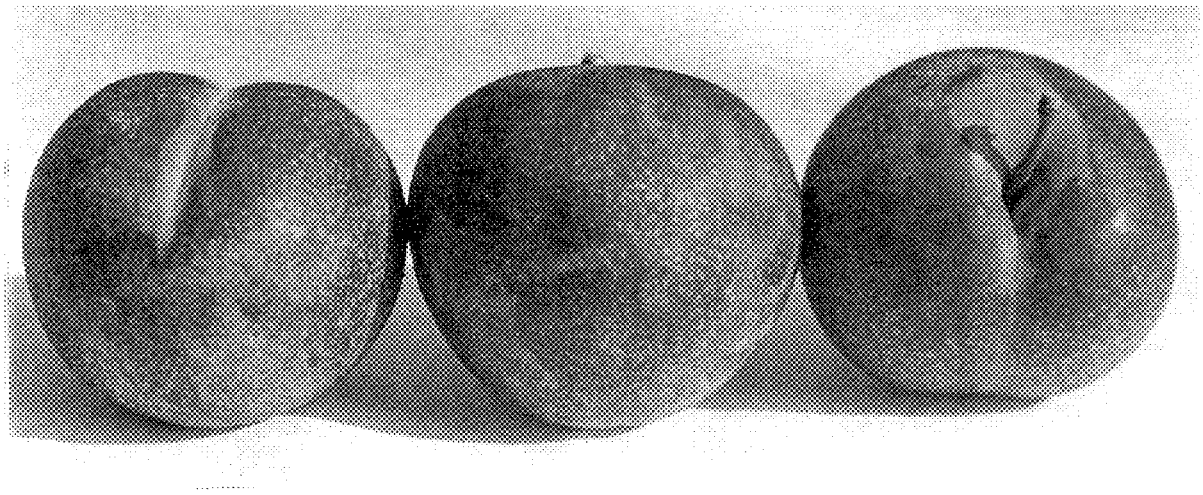
FIG. 2 depicts the fruit, whose illustration was taken shortly after being picked (firm ripe) and the colors are as nearly true as is reasonably possible in a color representation of this type.
Figure 3:
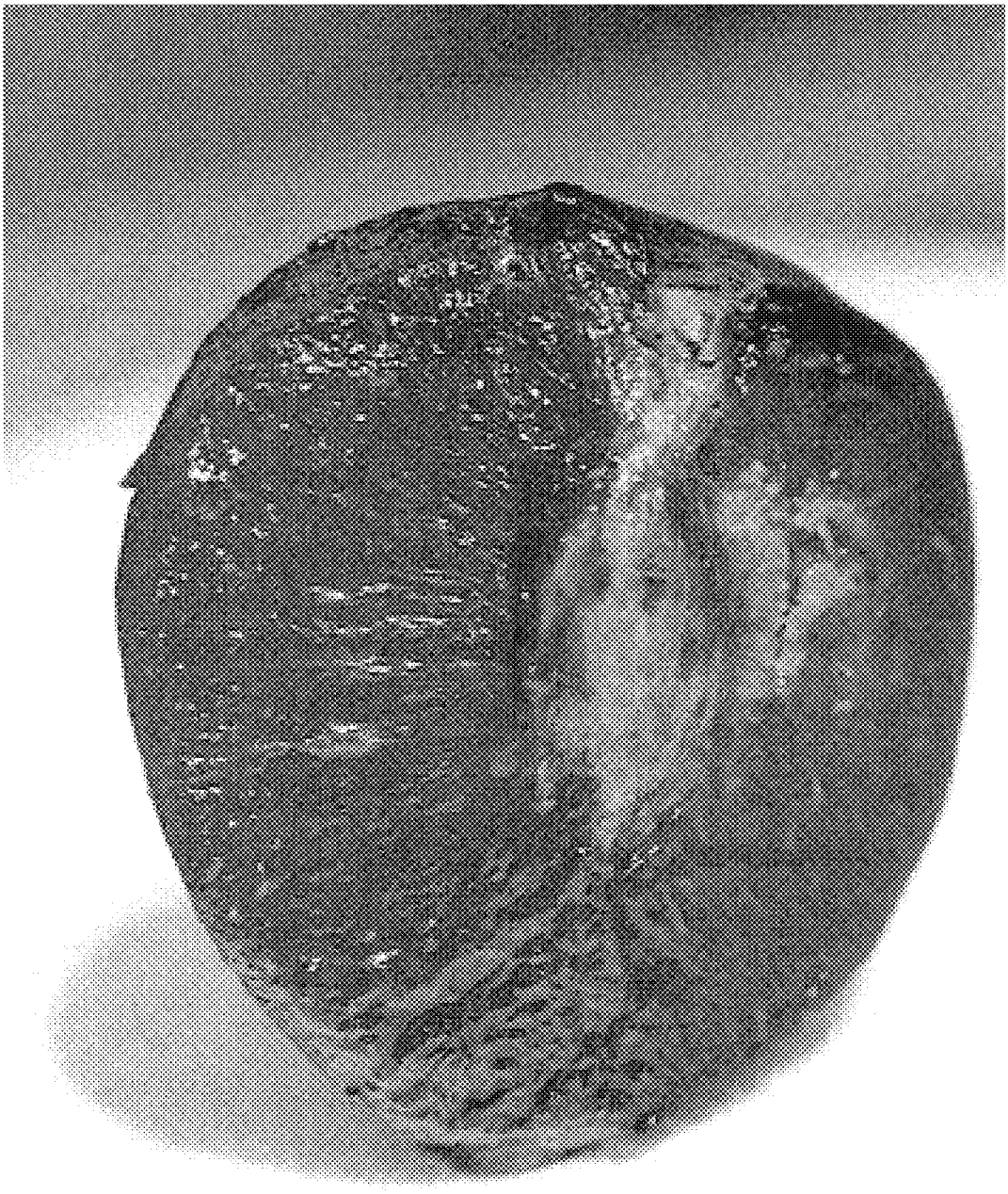
FIG. 3 shows a fruit divided in its suture plane to reveal flesh coloration, and a stone remaining in place.
Figure 4:
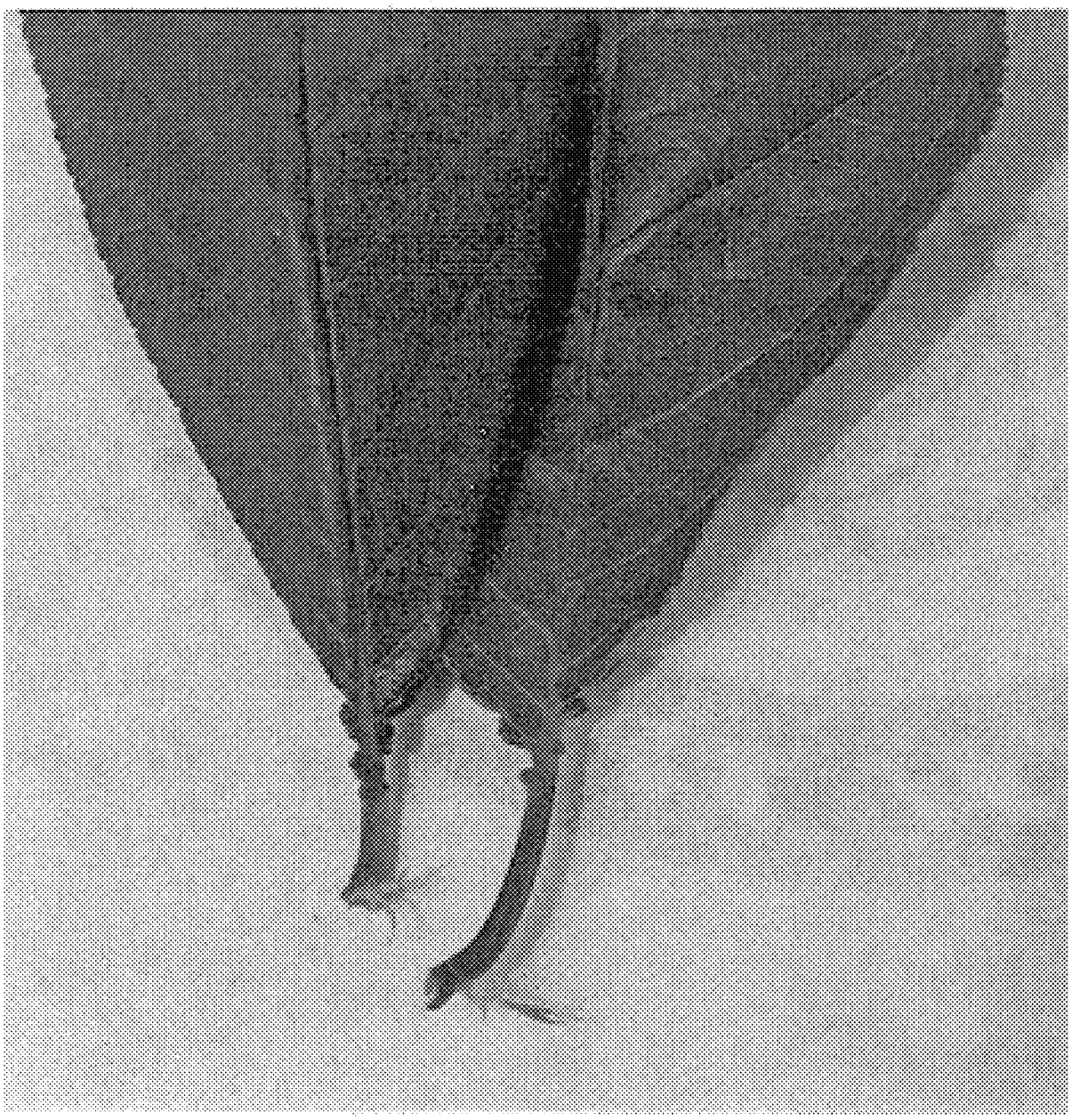
Figure 5:
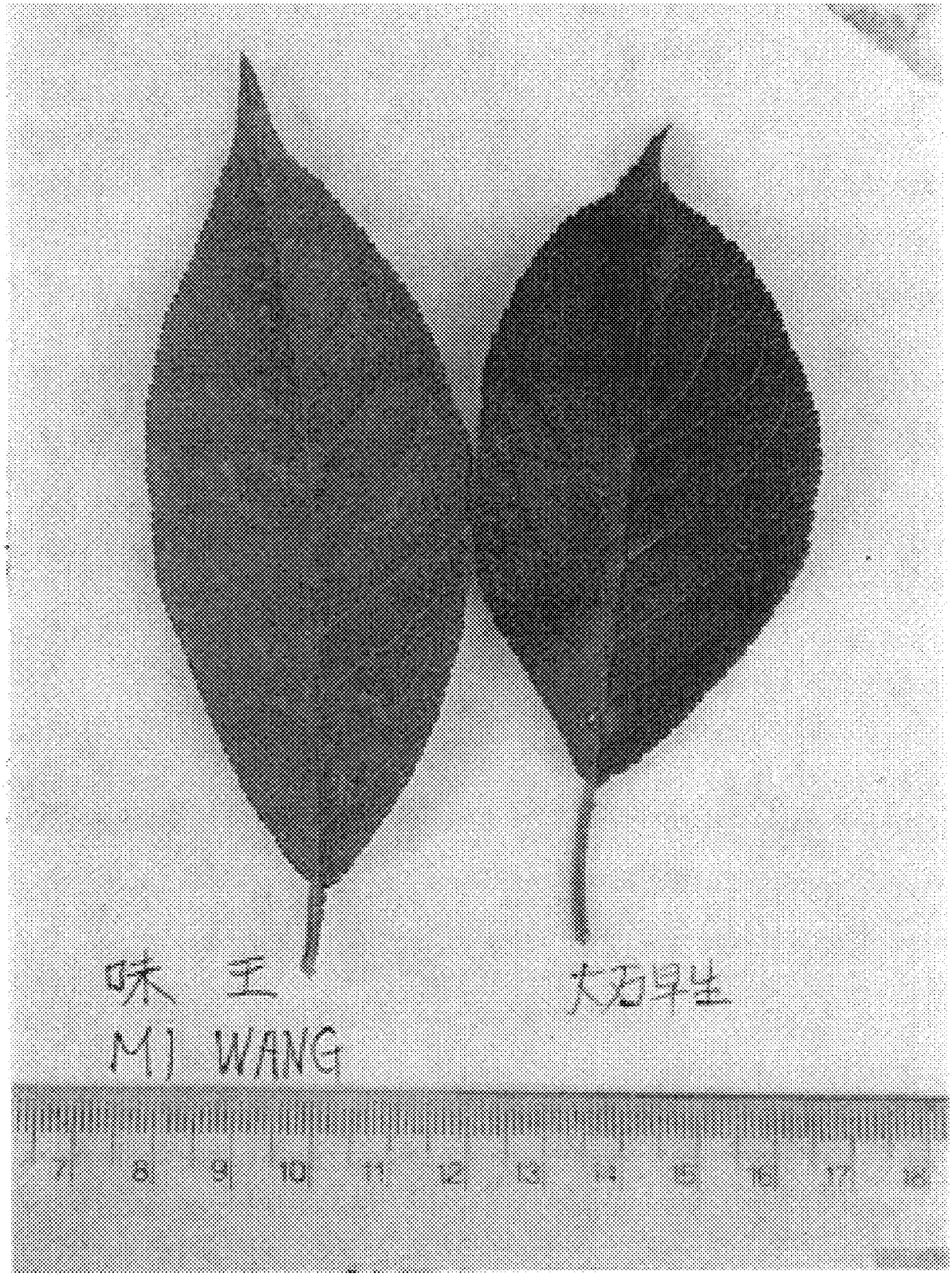

FIG. 4 shows the shape of a leaf of the new plumcot on the left and of a native plum leaf on the right, wherein the width of the plumcot leaf is narrower than that of the native plum leaf; and FIG. 5 shows a leaf blade of the present plumcot (left) and a plum (right), wherein the leaf blade of the present plumcot is smoother than that of the native plum near the leaf stalks and the leaf stalk of the present plumcot is shorter than that of the native plum leaf stalk.

The colors in the photographs are as nearly true as is reasonably possible in color representations of this type.

DESCRIPTION OF THE VARIETY

The following is a detailed botanical description of the new and distinct variety of plumcot tree, its fruit and foliage as based on observations of the specimen grown in my orchard located in JungPyong, KeoSan, ChungBuk, Korea with color terminology (except those in common terms) in accordance with PANTONE® Professional Color System Selector (Pantone, Inc., 1984, 1990).

Tree:
- *Size.*—Medium.
- *Vigor.*—Medium.
- *Form.*—Half open in shape.
- *Production.*—Productive.
- *Bearing.*—Regular.

Trunk:
- *Size.*—Medium to stocky.
- *Texture.*—Medium rough.
- *Color.*—Grayish Brown to dark Brown (19-1317) to (19-1116).

Branches:
- *Size.*—Medium.
- *Texture.*—Smooth.
- *Lenticels.*—Small to medium size. Medium number.
- *Color.*—Red Brown to dark Brown (19-1338) to (19-1322).

Leaves:
*Size.*—Medium. Narrow and long.
*Average length.*—8 to 10 cm.
*Average width.*—3.8 to 5.5 cm.
*Form.*—Oblanceolate.
*Texture.*—Smooth.
*Thickness.*—Medium.
*Margin.*—Finely serrate.
*Petiole.*—Medium length — about 2.65 cm. Medium thickness — about 0.16 cm.
*Glands.*—Average number 2. Usually located on base of leaf blade and on upper portion of petiole.
*Color.*—Upper surface green to dark green (18-0117) to (18-0322). Lower surface dull green to grayish green (17-6319) to (17-0119).

Flower buds:
*Size.*—Medium.
*Form.*—Plump.
*Length.*—Medium to short.

Flowers:
*Size.*—Medium.
*Blooming period.*—Apr. 10, 1996 to Apr. 15, 1996 in Chungbuk, Korea and April 15 to April 25 in Kangwon, Korea. Varies slightly due to climatic conditions.
*Color.*—White.
*Pistil.*—Pubescent.

Fruit:
*Maturity when described.*—Firm ripe.
*Date of first picking.*—Jul. 22, 1996.
*Date of last picking.*—Jul. 28, 1996.
*Weight.*—Average 80 to 100 g.
*Form.*—Globose — slight tip at apex and slightly flattened on stem end.
*Suture.*—Shallow. Nearly smooth. Extends from base to apex.
*Ventral surface.*—Nearly rounded, very slightly lipped a the stem end.
*Apex.*—Varies from rounded to slight pistil point.
*Base.*—Retuse.
*Cavity.*—Rounded to slightly elongated in suture plane. Average depth — 1.2 cm. Average breadth 12 cm.

Size:
*Thickness.*—Medium.
*Texture.*—Medium.
*Tendency to crack.*—None.
*Down.*—Scant.
*Color.*—Red (18-1660) to (18-1655) overspread with yellowish spots (14-0850) to (13-939).

Flesh:
*Texture.*—Firm but delicate. Intermediate between plum and apricot.
*Ripens.*—Evenly.
*Fibers.*—Small, tender.
*Juice.*—Moderate.
*Flavor.*—Excellent, mild, very sweet.
*Aroma.*—Moderate.
*Eating quality.*—Excellent.
*Amygdalin.*—Undetected.
*Color.*—Purplish red to dark red approximately (19-1626), Pit cavity — dark red (19-1716). Color extends from pit outward into flesh, heavier near apex.

Stone:
*Type.*—Semi-clingstone.
*Size.*—Very small. Average length 1.7 cm. Average breadth 1.0 cm. Average thickness 0.5 cm.
*Form.*—Ovoid.
*Base.*—Mostly straight — some rounded.
*Apex.*—Acuminate.
*Surface.*—Irregularly furrowed toward apex, ridges usually rounded, pitted toward base.
*Tendency to split.*—None.
*Color.*—Brown to reddish brown (18-1540) to (19-1540).

Use: Dessert.
*Market.*—Local and long distance.
Keeping quality: Good.
Shipping quality: Good.

The new and distinct variety of plumcot tree, its foliage and fruit described above may vary in slight detail due to variations in climate, soil conditions and cultural practices under which the variety may be grown. The botanical description above is that of the variety grown under the ecological conditions prevailing near JungPyong, KeoSan, ChungBuk, Korea.

I claim:

1. A new and distinct variety of plumcot (apricot×plum) tree, substantially as illustrated and described, characterized by its medium size, half open growth and being a regular and productive bearer of medium sized, middle to late season maturing, purplish red to dark red flesh, semi-clingstone fruit with excellent flavor and eating quality; the fruit is further characterized by having firm flesh, good handling and shipping quality and having a red ground color skin overspread with attractive yellowish spots; and characterized by the fruit having a very small stone.

* * * * *